United States Patent [19]

Pemberton et al.

[11] 4,278,173

[45] Jul. 14, 1981

[54] COMBINED PLUG AND AIR WARP NECK FINISH GAUGE

[75] Inventors: Ernest H. Pemberton; John J. Pezzin, both of Toledo, Ohio; Darius O. Riggs, Ottawa Lake, Mich.; Thomas B. Sorbie, Toledo, Ohio

[73] Assignee: Owens-Illinois, Inc., Toledo, Ohio

[21] Appl. No.: 73,596

[22] Filed: Sep. 10, 1979

[51] Int. Cl.³ ............................................. B07C 5/34
[52] U.S. Cl. ................................ 209/522; 33/178 R; 209/532
[58] Field of Search .............. 209/522, 523, 530, 531, 209/532, 600, 601, 604; 33/178 R, 178 F

[56] References Cited

U.S. PATENT DOCUMENTS

| | | | |
|---|---|---|---|
| 2,352,091 | 6/1944 | Fedorchak et al. | 209/532 |
| 2,596,342 | 5/1952 | McNutt et al. | 209/532 |
| 2,606,657 | 8/1952 | Berthelsen | 209/532 |
| 3,247,964 | 4/1966 | Doud et al. | 209/531 |
| 3,489,275 | 1/1970 | Powers, Jr. | 209/523 |
| 3,717,248 | 2/1973 | Scribner | 209/523 |
| 3,914,872 | 10/1975 | Strzala | 209/531 X |

Primary Examiner—Robert J. Spar
Assistant Examiner—Edward M. Wacyra
Attorney, Agent, or Firm—D. T. Innis; M. E. Click; D. H. Wilson

[57] ABSTRACT

There is described a plug and air warp gauge which takes the form of an elongated vertically, reciprocated gauging head that is mechanically driven under the influence of a rotating cam. Coaxially within an annular head is positioned a plug which has a diameter such that it will pass through an unchoked neck of a bottle. The plug is attached to the lower end of a tube which is coaxially positioned within a larger tube. The larger tube is raised and lowered mechanically and when in its uppermost position, will support the plug-carrying tube. When the larger tube is lowered, the plug tube also is lowered. The lower end of the larger tube is in the form of an annular piston which will move downward within a cylinder that seats on the bottle finish. As the annular piston moves down, it will pressurize the inside of the bottle and the cylinder if the seal with the finish of the bottle is good. After the arrival of the larger tube at its lowest position, both the pressure generated in the bottle and cylinder and the position of the plug tube are observed for determining the presence or absence of a defective bottle.

7 Claims, 7 Drawing Figures

COMBINED PLUG AND AIR WARP NECK FINISH GAUGE

BACKGROUND OF THE INVENTION

It has been the practice in the past to gauge the internal neck diameter of containers by the insertion of a plug of specific diameter into the neck. In those instances where the plug would not pass into and through the neck of the container, the container would be termed as having a "choked finish" or neck. One example of such a gauge is that of U.S. Pat. No. 2,596,342 in which a plurality of inspection or plug gauging heads are carried by a unit positioned above a moving conveyor wherein the conveyor carries the bottles in series beneath the plurality of gauging units. It was necessary to have an inspection device composed of a plurality of gauging units in order to inspect containers at the rate in which they were being produced by forming machines. It was expected that one multiple head plug gauge would be positioned at the cold end of the lehr that is being used to anneal the containers that are made by machines. In the past, there would be perhaps a flow of 180 bottles a minute being gauged. The present-day bottle lines now are running at even greater speeds and volume, such that a gauge capable of handling up to 400 or so bottles per minute would be highly desirable.

In addition to the known plug gaugers in the prior art, there is a need for a high speed apparatus which will also determine whether or not the neck or finish portion of the container has been completely formed. As has occurred during the production of glassware, sometimes the finish is unfilled, meaning that during the formation of the neck of the container, it was not completely formed in the neck ring. When an unfilled finish is produced, the upper rim surface of the neck of the container will not be complete. Obviously, when this condition occurs, the application of a closure to a filled container will not properly seal on the upper rim surface of the container and will result in a "leaker". Therefore, this possible defect in a container should be inspected for and obviously the defective container removed from the production line. This inspection, preferably, takes place in the glass container plant where the bottles are made. It may be desirable to inspect return bottles which come back to a bottling plant with the neck of the bottle chipped such that it would also produce an unsealed container when the closure is applied. It can be understood that a chipped finish would be somewhat analogous to an unfilled finish in a newly formed bottle. Thus a gauge for inspecting glass containers for "unfilled finishes" may also be used to inspect bottles that have been returned for refilling.

Containers in the past have been examined for unfilled finishes by optical means as shown in U.S. Pat. No. 3,176,842. "Unfilled finishes" are somewhat similar to the defect termed "line-over-finish" which is produced during the manufacture of containers. The "line-over-finish" was caused usually by a blister or bubble, entrapped within the molten glass, being forced into the neck area during "settle blow" and resulting in the blister opening out at the surface of the neck as an elongated void. These defects are more fully described in the above-referred-to patent and also have been inspected by mechanical feeler-type gauges, an example of which is shown in U.S. Pat. No. 3,414,127.

SUMMARY OF THE INVENTION

The present invention provides apparatus for simultaneously gauging the internal diameter of the necks of bottles and detecting the presence of unfilled finishes in which a gauging head positioned above the container at a specified position is mechanically lowered so that an elongated plug carried by the head will move downwardly through the neck opening of a glass container having acceptable size. At the same time, an annular collar which surrounds the plug will be permitted to seat upon the upper finish of the container by the action of a spring and continued downward movement of the head will cause internal pressure to build up within the confines of a cylinder which is communicating with the interior of the container and sealed by the annular collar. Internal pressure thus builds up within the container if, in fact, the container finish is completely formed. Means are provided for indicating the movement of the plug through the neck of the container and also the reaching of a predetermined level of pressure on completion of the downward stroke of the mechanism for operating the gauging head.

DETAILED DESCRIPTION OF THE DRAWINGS

Generally speaking, the present invention will be used in connection with a multiple station bottle-handling system wherein the containers to be inspected will be subject to a number of inspections at a plurality of stations. An example of such a handling system is shown in U.S. Pat. No. 3,383,483 wherein the containers are brought to an indexing starwheel by a moving conveyor. The starwheel is provided with pockets within which the containers will seat and then the containers are laterally transferred by the starwheel from the entrance conveyor through a number of positions, one of which would be a position at which the present invention would be situated. The starwheel would carry the container to be inspected into and out of the station where the present plug gauging and filled finish inspection is to be carried out.

Figure 1:
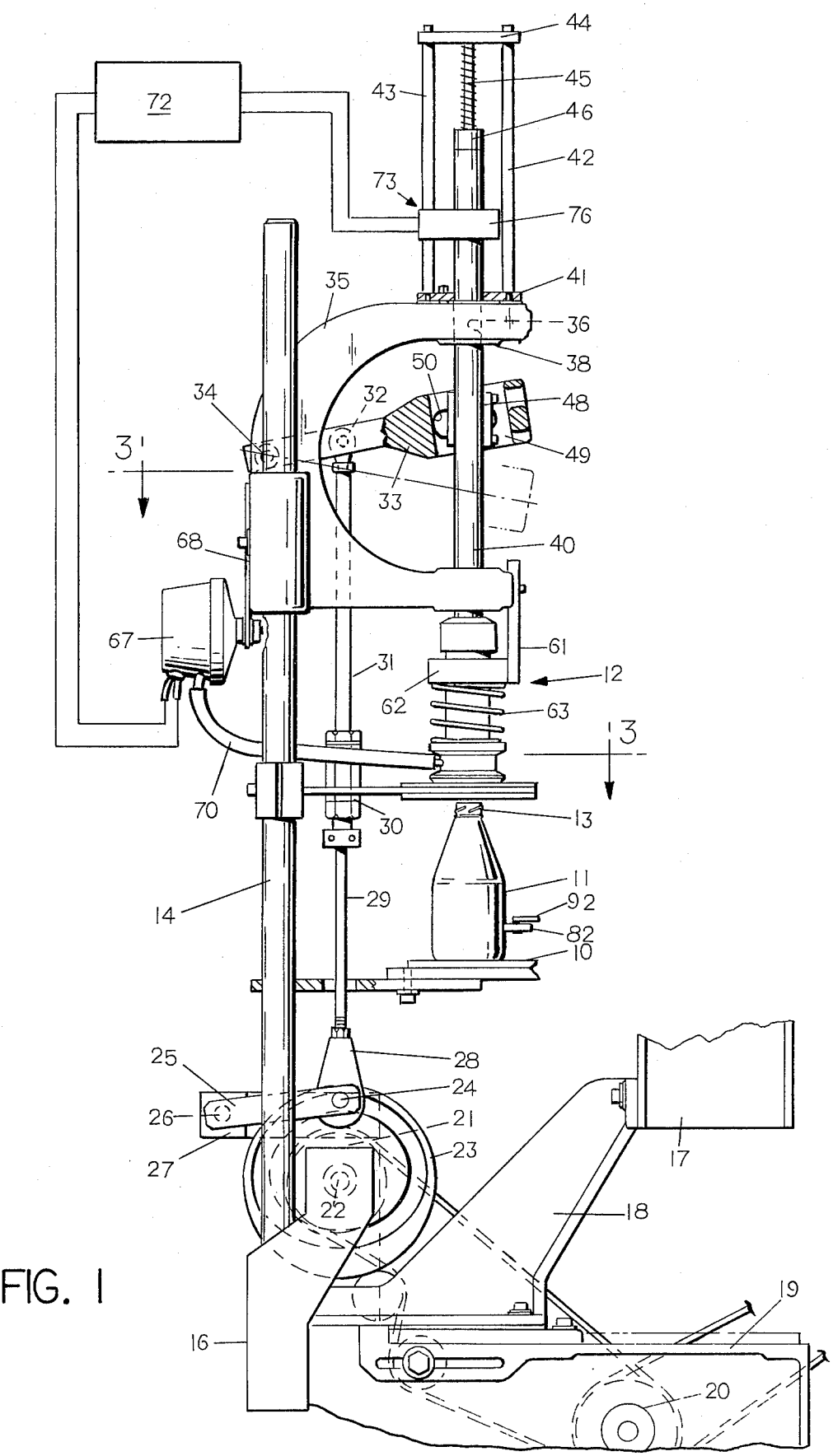
FIG. 1 is a side elevational view, partly in section, of the apparatus of the invention.

With particular reference to FIG. 1, there is shown a surface 10 upon which a container 11 is positioned. The container 11 is in the position to be inspected and the inspection apparatus takes the form of a gauging head, generally designated 12, positioned axially above the finish portion 13 of the container. The gauging head 12 is supported by a pair of vertically extending posts 14 and 15. The lower ends of the posts 14 and 15 are mounted within a stationary bracket 16, it being understood that the bracket 16 is mounted to a lower beam 17 and casting 18 which are supported from the floor by a frame 19, only the upper portion of which is shown.

The frame 19 houses a driven pulley 20. A second pulley 21, connected to a shaft 22, drives a box cam 23. The shaft 22 is supported by the bracket 16. Positioned in the box cam will be a follower 24 mounted at the free end of a pivoted arm 25. The other end of the arm 25 is pivoted at 26 to a stationary bracket 27. The follower 24 is also connected to a clevis 28 which is threadably connected to the lower end of a rod 29. The rod 29 is connected at its upper end to a connector 30 which in turn carries a rod 31, to the upper end of which is threaded a clevis 32. Clevis 32 is pivotally connected to an operating arm 33 which is pivoted at its left-hand end by a pin 34 extending through and between two arms 35 which are supported by the posts 14 and 15. The arms 35 extend to the right, as viewed in FIG. 1, and at their extending ends are joined together and provided with vertical openings 36 and 37 within which are positioned sleeve bearings 38 and 39 respectively. The sleeve bearings 38 and 39 serve as bearings for a vertically extending tube 40.

Adjacent the upper end of the tube 40, which extends through the sleeve bearing 38, is a cross-head 41. The cross-head 41 supports a pair of vertically extending rods 42 and 43 which support a second cross-head 44 therebetween at the upper ends thereof. At the center of the cross-head 44 there is connected a downwardly extending, vertical shaft 45. The shaft 45 extends downwardly through a central opening in a cap 46 which is mounted at the upper end of a tube 47. The tube 40, intermediate the tube bearings 38 and 39, carries a clamp 48. The clamp 48 carries a pair of rollers (not shown). The operating arm 33 has a central opening 49 formed therein within which the clamp 48 is positioned. The arm 33, in the area of the opening 49, is provided with a pair of elongated slots 50. Within the slots 50, only one of which is shown, are positioned the rollers carried by the clamp 48. In this manner, operation of the operating arm 33 by the rod 31 will result in reciprocation of the tube 40 in a vertical direction, it being understood that the actual movement is between the full line position shown in FIG. 1 to the dotted line position shown in FIG. 1. The full line position shown in FIG. 1 is that where the tube 40 is in its most elevated position, at which time the cap 46 of the tube 47 is resting upon the upper end of the tube 40. Within the tube 47, a relatively weak spring 91 is positioned and extends from beneath the cross-head 44 to the lower end of the tube 47. This spring functions to provide a light downward force on the plug-carrying tube 47.

Figure 2:
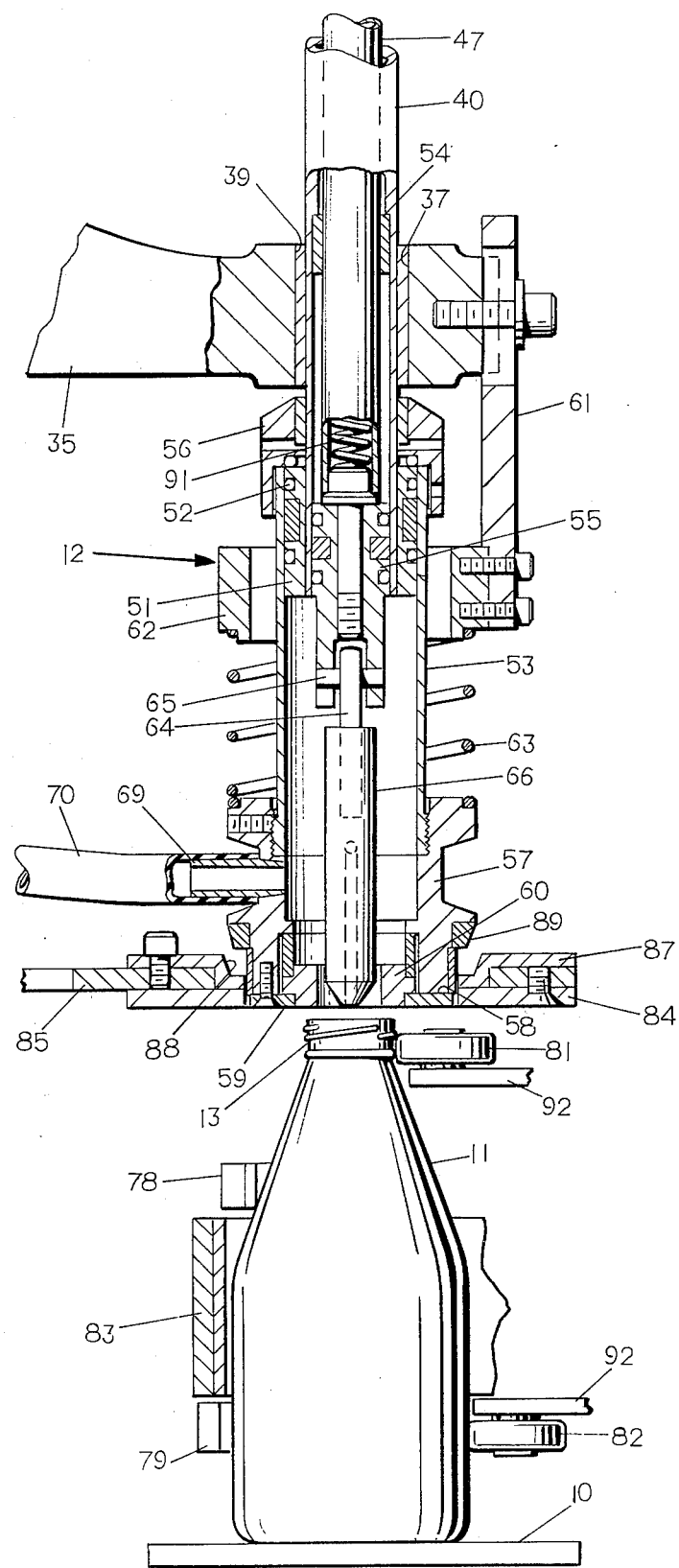
FIG. 2 is a vertical, sectional view through the lower portion of the gauging head of FIG. 1.

With reference to FIG. 2, the internal details of the gauging head will be explained. As can be seen in viewing FIG. 2, the lower end of the tube 40 carries a piston 51 which is welded thereto adjacent the end thereof. The piston 51 has the usual O-ring seals 52 between the outer surface thereof and a cylinder 53. The tube 40 additionally is provided internally with a sleeve bearing 54 which serves as a guide for the tube 47. The lower end of the tube 47 carries a piston 55 which also is provided with O-rings and seals, it being understood that the piston 55 moves relative to the tube 40, but is sealingly engaged therewith so as to prevent the movement of air upward through the tube 40 past the piston.

In the position shown in FIG. 2, the gauging head 12 is in its uppermost position wherein the tube 40 has been elevated such that its piston 51 is in engagement with a cylinder-supporting member 56. The lower end of the cylinder 53 is connected to an annular member 57. Lower rim 58 of the annular member 57 is provided with a retaining ring 59. The retaining ring 59 holds a rubber or other compressible material ring 60 within the confines of the interior of the member 57. The fuction of this compressible material ring 60 is to seat upon the finish or upper rim surface of the container 11 when the head 12 is lowered. The arm 35 has bolted thereto a downwardly extending bracket 61, to the lower end of which is connected a ring 62. The ring 62 is provided with a stepped notch in the bottom thereof within which the upper end of a coil spring 63 is seated. The lower end of the coil spring 63 seats within a similar notched area formed in the upper surface of the member 57. The spring 63 is of sufficient force that it will, when the cylinder 53 is permitted to be lowered, seat the ring 60 on the finish of the bottle in sealing contact therewith. When the tube 40 is lowered by the arm 33, the tube 47 will also move downwardly with the tube 40 to the extent that it is permitted to move.

Figure 6:
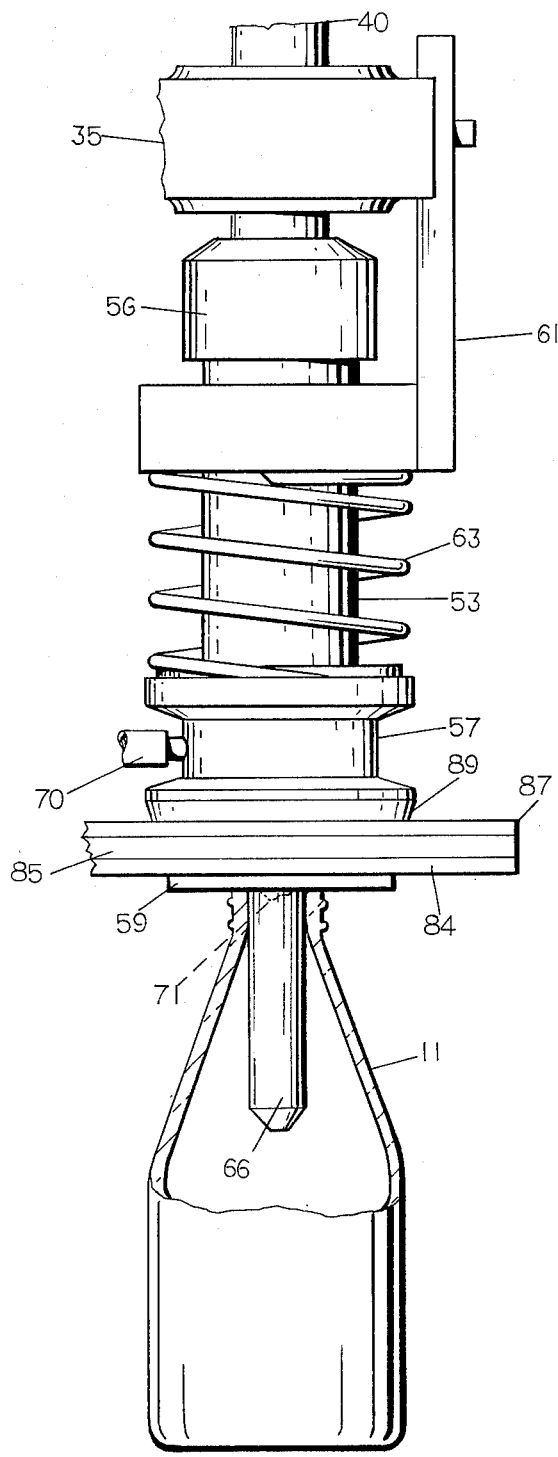
FIG. 6 is a view similar to FIG. 4, showing the plug as it would appear in an acceptable container.

As can be seen when viewing FIG. 2, the piston 55 has a downwardly extending portion which is bifurcated. Within this bifurcated portion is positioned a tongue 64, with the tongue being held in the bifurcated portion of the piston 55 by a pin 65. The tongue 64 supports a gauging plug 66. Thus it can be seen that when the tube 40 is lowered and the tube 47 moves therewith, since the upper end of the tube 47 has its cap 46 moving with the upper end of the tube 40, the plug 66 will enter through the neck of a container being inspected. In the event the container neck is of a dimension sufficient to pass the plug unimpeded, the plug will assume a position within the container, as illustrated in FIG. 6 and at the same time, the tube 40 will have been lowered a specific distance to its lowest point. When the cylinder 53 has its ring 60 seated upon the finish of the container, cylinder 53 will stop its downward descent. However, the tube 40 and its piston 51 will continue downwardly and at this time air, which is entrapped within the cylinder 53 and the interior of the container, will become compressed and the pressure build-up within the cylinder 53 and within the interior of the container 11 may be indicated by an indicator 67 mounted at the left side of the post 14 by a bracket 68, by reason of the fact that a side-opening port 69 in the member 57 is connected to the gauge by a flexible tube 70.

In actual practice, the indicator 67 may take the form of a pressure actuated switch which may either be opened normally and then closed when a particular pressure level is reached or, vice versa, could be a closed switch which is opened when a predetermined pressure is achieved. In the event that the finish of a container is not filled, as is illustrated in FIG. 6 at 71, there will not be a pressure build-up within the member 57 and thus the indicator 67 will not respond and the container will thus be considered to be defective as having an "unfilled finish".

As shown in FIG. 1, the indicator 67 is connected by wires to a control console 72. The console 72 is also connected by a pair of wires to a position-indicating device, generally designated 73. The device 73, as illustrated in more detail in FIG. 5, comprises a light-emitting diode 74 and a photocell 75 carried by a support bracket 76. The bracket 76 is adjustably fastened to the upright rod 43 in any suitable manner.

Figure 4:
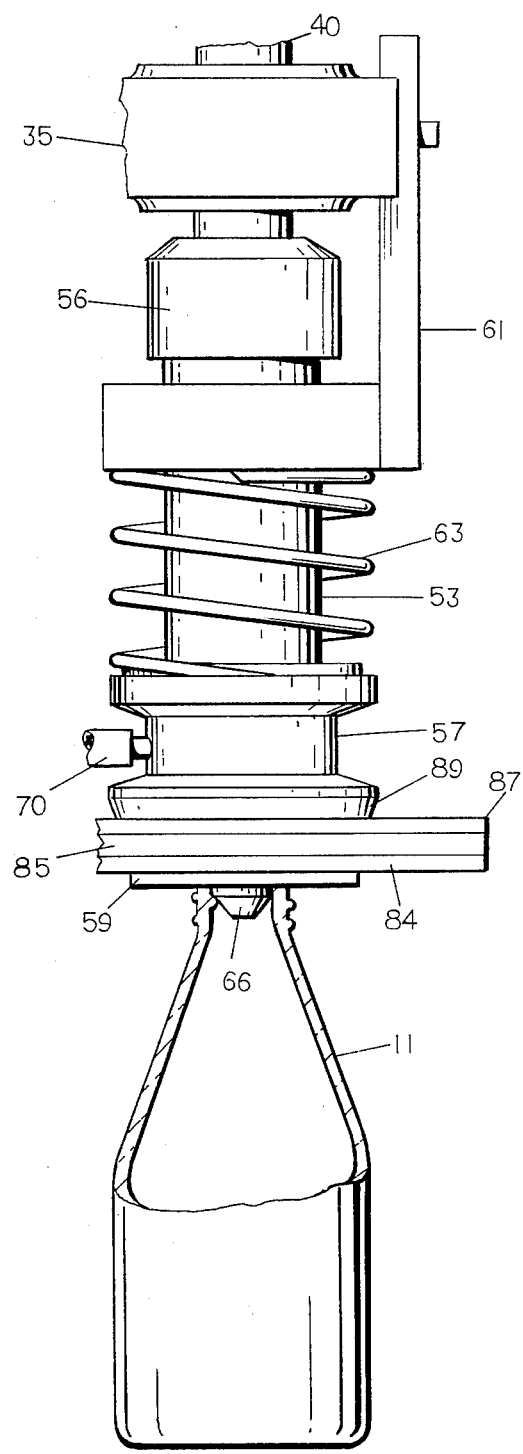
FIG. 4 is an enlarged view of the lower portion of the gauging head of FIG. 1, showing the position of a plug encountering a choked neck.
Figure 7:
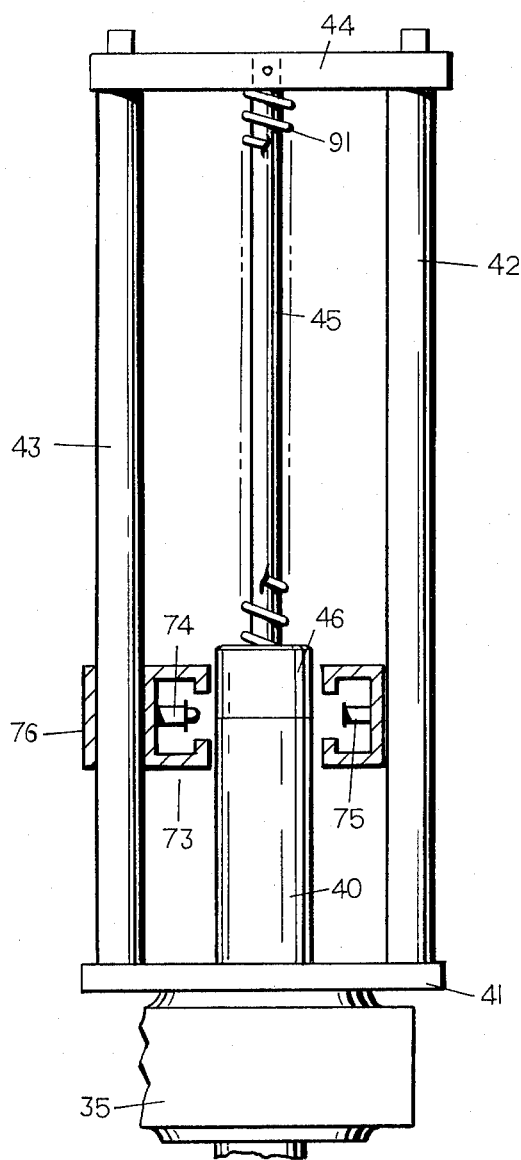
FIG. 7 is a side elevational view, similar to FIG. 5, showing the position of the plug-supporting tube relative to the piston-supporting tube in the situation of FIG. 6.
Figure 5:
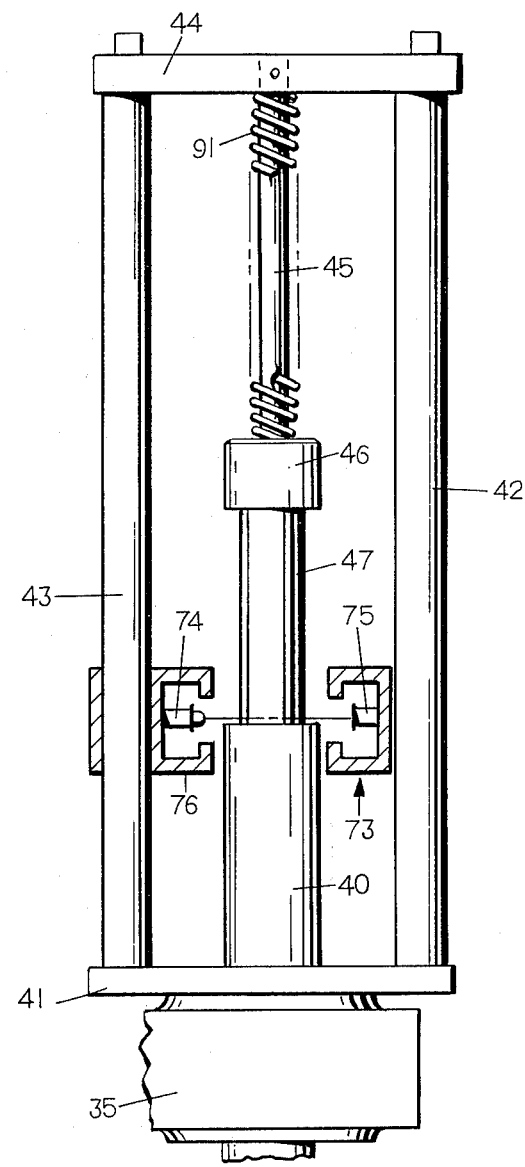
FIG. 5 is a side elevational view, partly in section, of the upper structure showing the relative positions of plug-supporting and piston-supporting tubes when the lower portion of the plug is in the position of FIG. 4.

With particular reference to FIGS. 4 and 5, the situation which may occur when the plug encounters a choked neck, is illustrated. As can be seen, the plug 66 in FIG. 4 has been stopped within the neck of the container 11. Continued downward movement of the tube 40 will occur; however, the tube 47 and its cap 46 will stop any downward movement and at the time that the pressure within the container is to be gauged, the upper end of the tube 40 will have reached its lowermost position, as illustrated in FIG. 5. However, the cap 46 of the tube 47 will remain in an elevated position. The light-emitting diode 74 and the photocell 75 are positioned such that the beam of light which will extend between the two elements will pass the tube 47. Thus when a choked neck is encountered, the photocell 75 will receive illumination from the diode 74, as illustrated in FIG. 5. In the situation where there is no choked neck, the cap 46 will move downward with the tube 40 to the position shown in FIG. 7. The cap 46 is of such a diameter that the beam from the diode 74 will not reach the photocell 75 because the cap will block the light path.

In actual practice, the diode will be fired at the time that the tube 40 reaches its lowermost position, this being indicated by the tripping of a switch (not shown). At this time, the pressure will be gauged and both signals fed to the console 72. The console 72 may then be used as an indicator or it may provide a signal to a reject mechanism which would then automatically reject a defective container at some later point in its movement through the bottle-handling machine.

Figure 3:
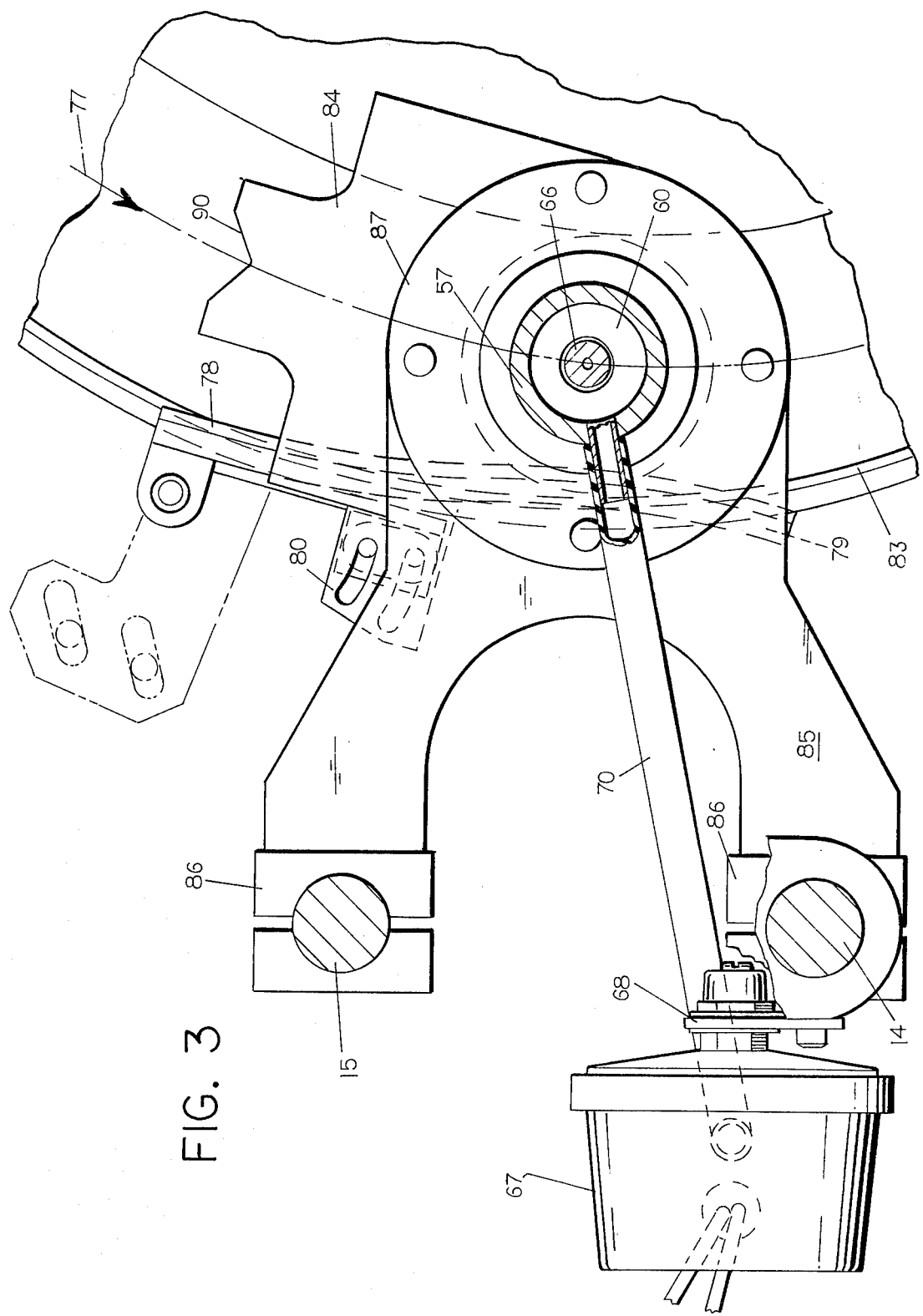
FIG. 3 is a cross-sectional view taken at line 3—3 of FIG. 1.

The gauging head 12 is positioned at a fairly specific location, such that it is necessary that the containers which are being brought to the gauging head must be accurately positioned beneath in order for the gauge to function properly and with this in mind, and with particular reference to FIGS. 2 and 3, it can be seen that when the bottles are moved in the direction of the arrow 77 on FIG. 3, the shoulder portion will be engaged by a rail 78. This rail 78 may be adjusted so as to provide the close guidance required. In addition, a lower rail 79, which will engage the side of the bottle, may also be adjusted, as shown by an adjustable mount 80, so as to accurately position the bottle at the time it is to be gauged. Rollers 81 and 82 are carried within the pockets of the pair of spaced starwheels 92 which are handling the containers, it being understood that the containers are generally guided in their movements with the starwheel by an outside rail 83. The member 57, with its ring 60, is movable downward to a limited extent to seat or seal against the upper bottle finish. A stripper plate 84, having a center opening formed therein, of a size sufficient to permit the movement of the member 57 to move downwardly therethrough is positioned slightly above the expected height of the containers to be tested. The stripper plate 84 is carried by a Y-shaped support bracket 85, as best shown in FIG. 3. The bracket 85 in turn is supported by clamp blocks 86 to the posts 14 and 15. A circular plate 87 is fixed to the upper surface of the support bracket 85 and is provided with an inner, annular beveled shoulder 88. It will be noted that the shoulder 88 is complementary in configuration with a shoulder 89 formed of a cushioning material which surrounds the member 57. In the event the gauging head 12 is operated at a time when there is no bottle present at the position to be gauged, the member 57 will only be lowered to the extent permitted by the shoulder 89 engaging the plate 87.

The function of the ring 60 is to assure, upon retraction of the vented plug, that the bottle not be carried upwardly and become entangled in the gauging mechanism. Additionally, the plate 84 protects the gauging head in that it has a modified dove-tail 90 facing in the direction of the incoming movement of the bottles so that if a tall bottle were to enter or attempt to enter beneath the stripper plate, the dove-tail 90 would engage the neck of the bottle and force the bottle down when entering the gauging position. In this manner, the gauging head is protected from accidental damage.

It thus can be seen that the present invention provides apparatus which will simultaneously gauge bottles for "choked necks" and "unfilled finishes" without the requirement of a separate source of air under pressure. The apparatus is capable of working at the speed of other gauging equipment that may be formed around the circumference of the bottle-handling starwheel. For example, U.S. Pat. No. 3,313,409, commonly owned with the present case, shows such an arrangement where the present invention would be used in place of the plug gauger disclosed therein at 50.

We claim:

1. Apparatus for simultaneously gauging the internal diameter and detecting the presence of unfilled or warped finishes of glass containers comprising:
    a reference surface for supporting a container in an upright attitude;
    a gauging head positioned axially above the neck of the container to be gauged;
    means connected to said head for raising and lowering the head with a predetermined amplitude of movement;
    said gauging head including an elongated plug having a predetermined external diameter adapted to pass through the neck opening of a glass container of acceptable size;
    an annular collar surrounding said plug and adapted to move downward into sealing engagement with the top surface of the neck or finish of the container under test;
    a first, vertically reciprocated, tube connected to the upper end of said plug;
    a second, vertically reciprocated, tube surrounding said first tube;
    an annular piston formed at the lower end of said second tube;
    a cylinder connected to said annular collar, within which said annular piston is slideable; and
    means connected to said cylinder for measuring the pressure produced therein by movement of said piston with the collar sealed to the container finish as an indication of the integrity of the sealing surface of the container.

2. The apparatus of claim 1, further including means for indicating the movement of the first tube a predetermined amount relative to the second tube.

3. The apparatus of claim 2, wherein said means for indicating relative movement of said tubes comprises a light-emitting diode, a photo detector positioned opposite said light-emitting diode, means for mounting said light-emitting diode and detector as a unit at a position immediately above the level of the upper end of said second tube when in its lowest position.

4. The apparatus of claim 3, further including a cap fixed to the upper end of said first tube and having a diameter similar to the diameter of the second tube and normally resting thereon, said light-emitting diode and detector being positioned with its line of sight interrupted by the cap on said first tube when the first tube travels with the second tube and uninterrupted when the first tube is caused to stop in its descent before the second tube is stopped.

5. The apparatus of claim 1, wherein said first tube is formed with a piston portion intermediate its length, said piston portion sealingly engaging the interior of said second tube.

6. The apparatus of claim 1, wherein said annular collar comprises an annular metal member and a flexible sealing ring secured to the lower part of said collar and adapted to seat on the finish of the container.

7. The apparatus of claim 1, wherein said means for measuring the pressure comprises a gauge mounted on a fixed support, a duct opening into the side of said collar and a flexible conduit extending between the gauge and the duct.

* * * * *